(12) United States Patent
Waser et al.

(10) Patent No.: US 10,856,391 B2
(45) Date of Patent: Dec. 1, 2020

(54) METHOD TO CORRECT SIGNAL LIGHT INTENSITIES MEASURED BY A DETECTOR OF A DETECTION UNIT IN A LABORATORY INSTRUMENT

(71) Applicant: Roche Molecular Systems, Inc., Pleasanton, CA (US)

(72) Inventors: Patrick Waser, Lucerne (CH); Florian Betschart, Brunnen (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 16/543,933

(22) Filed: Aug. 19, 2019

(65) Prior Publication Data
US 2020/0068683 A1 Feb. 27, 2020

(30) Foreign Application Priority Data
Aug. 22, 2018 (EP) .................................. 18190123

(51) Int. Cl.
*H05B 47/11* (2020.01)
*H05B 47/10* (2020.01)
(Continued)

(52) U.S. Cl.
CPC ................ *H05B 47/11* (2020.01); *B01L 9/56* (2019.08); *G01N 21/274* (2013.01); *G01N 33/48* (2013.01); *G01N 2201/12746* (2013.01)

(58) Field of Classification Search
CPC ............. H05B 37/0218; H05B 39/042; H05B 39/081; H05B 39/083; H05B 41/325;
(Continued)

(56) References Cited

U.S. PATENT DOCUMENTS 5,888,455 A 3/1999 Seaton et al.
8,274,650 B2 9/2012 Tomaney et al.
(Continued)

FOREIGN PATENT DOCUMENTS

EP 2635897 B1 12/2015
EP 2162728 B1 7/2016
(Continued)

OTHER PUBLICATIONS

European Search Report, Application No. 18190123.2; dated Nov. 12, 2018.

*Primary Examiner* — Henry Luong
(74) *Attorney, Agent, or Firm* — Maneesh Gupta; Pamela C. Ancona

(57) ABSTRACT

A method to correct signal light intensities measured by a detector of a detection unit in a laboratory instrument is presented. The detection unit comprises a light source, a sample plane comprising a sample holder configured to hold at least one sample vessel comprising a test sample to be illuminated, a reference light sensor, and the detector. Based on a basic light intensity of a newly manufactured light source and an initial light intensity measured by the reference light sensor the sensitivity of the reference light sensor can be determined. And signal light intensities measured by the detector can be corrected based on the determined sensitivity and subsequently measured reference light intensities of the reference light sensor in order to generate comparable test results.

15 Claims, 6 Drawing Sheets

(51) Int. Cl.
  *B01L 9/00* (2006.01)
  *G01N 21/27* (2006.01)
  *G01N 33/48* (2006.01)

(58) Field of Classification Search
  CPC ..... H05B 41/3922; B01L 9/56; G01N 21/274; G01N 33/48; G01N 2201/12746
  See application file for complete search history.

(56) References Cited

U.S. PATENT DOCUMENTS

| | | |
|---|---|---|
| 8,482,730 B2 | 7/2013 | Tomaney et al. |
| 9,956,559 B2 | 5/2018 | Cherubini et al. |
| 2003/0205681 A1* | 11/2003 | Modlin ............... G01N 21/6452 250/458.1 |
| 2009/0213371 A1 | 8/2009 | Goodyer et al. |
| 2013/0310268 A1 | 11/2013 | Christiansen et al. |
| 2016/0228876 A1 | 8/2016 | Chu et al. |
| 2016/0237474 A1 | 8/2016 | Marks |
| 2017/0146513 A1 | 5/2017 | Grimberg et al. |

FOREIGN PATENT DOCUMENTS

| | | |
|---|---|---|
| WO | WO0240971 A1 | 5/2002 |
| WO | WO2008156669 A1 | 12/2008 |
| WO | WO2009127424 A9 | 2/2010 |

\* cited by examiner

METHOD TO CORRECT SIGNAL LIGHT INTENSITIES MEASURED BY A DETECTOR OF A DETECTION UNIT IN A LABORATORY INSTRUMENT

CROSS-REFERENCE TO RELATED APPLICATION(S)

This application claims the benefit and priority of European Application Serial No. 18190123.2, filed Aug. 22, 2018, which is incorporated herein by reference.

FIELD OF THE DISCLOSURE

The present disclosure belongs to the field of in vitro diagnostic test sample analysis. Within this field, it relates to a method, a laboratory instrument, a computer program product, and a computer-readable medium for correcting signal light intensities measured by a detector of a detection unit in a laboratory instrument.

BACKGROUND

In diagnostic laboratory environments multiple laboratory instruments of the same type may be installed for executing the same laboratory tests on test samples. The laboratory instruments may be installed within the same accommodation of a diagnostic laboratory, distributed over different accommodations of the diagnostic laboratory, or even distributed over different diagnostic laboratories. Test results generated by different laboratory instruments of the same type have to be reproducible and comparable to each other for reliable and consistent diagnosis. If, for example, a physician orders two equal laboratory tests he expects that both test results are comparable to each other although it might happen that the two laboratory tests are executed on two different laboratory instruments depending on their current workload.

Typically, laboratory instruments comprise means for detecting the presence and/or for determining the concentration of an analyte or parameter associated with an analyte of a test sample. In many well-known detection methods such as photometry, fluorometry, turbidimetry, nephelometry, luminescence measurement, fluorescence polarimetry, flame photometry, atomic absorption photometry, flow cytometry, coulter method, and imaging a detection unit of a laboratory instrument detects and measures light intensities of analyte-related signals. The measured signal light intensities are then processed to test results indicating the presence and/or the concentration of an analyte of interest in a test sample. However, test results may vary from laboratory instrument to laboratory instrument which may lead to a poor comparability and subsequent misinterpretation of test results generated on different laboratory instruments of the same type. Reasons for this test result variation between laboratory instruments may be that components of detection units such as the light source are subject to manufacturing tolerances and/or unequal deteriorations during operation. Accordingly, the brightness or intensity of the light source of a laboratory instrument may be monitored using for example reference channels. And the measured reference signals of the reference channels can be used to normalize measured signal light intensities as disclosed in U.S. Pat. No. 9,956,559B2. However, such reference channels may also be subject to large manufacturing tolerances and without calibration their reference signals cannot be used to correct measured signal light intensities on the basis of which absolute or quantitative test results are calculated. Another method for monitoring the light source of a laboratory instrument may be based on regular light intensity measurements by inserting a calibrated light sensor into the laboratory from time to time. However, such methods are time and cost intensive. Furthermore, no continuous monitoring of the light source is possible.

Therefore, there is a need to correct signal light intensities measured by a detector of a detection unit in a laboratory instrument in a simple, reliable, and cost-efficient way. It was an object of the present disclosure to improve conventional methods for reducing test result variations between different laboratory instruments of the same type, particularly to better serve the needs of automated in vitro diagnostic test sample analysis.

SUMMARY

The present disclosure discloses a method, a laboratory instrument, a computer program product, and a computer-readable medium for correcting signal light intensities measured by a detector of a detection unit in a laboratory instrument.

The present disclosure relates to a method to correct signal light intensities measured by a detector of a detection unit in a laboratory instrument. The laboratory instrument comprises the detection unit and a control device. The detection unit comprises a light source, a sample plane comprising a sample holder configured to hold at least one sample vessel comprising a test sample to be illuminated, a reference light sensor, and the detector. The light source is configured to emit light towards the sample plane. The reference light sensor is located in proximity to the sample holder and configured to measure an initial light intensity of emitted light towards the sample plane and at least one reference light intensity of emitted light towards the sample plane. The detector is configured to measure a signal light intensity of emitted light from the sample plane. The method comprises the following steps:

a) the control device receives a basic light intensity of the light source b) the control device activates the light source in the detection unit c) the reference light sensor measures an initial light intensity of emitted light towards the sample plane and transmits the measured initial light intensity to the control device d) the control device calculates a sensitivity of the reference light sensor based on the measured initial light intensity and the basic light intensity of the light source e) the detector measures at least one signal light intensity of emitted light from the sample plane and transmits the at least one measured signal light intensity to the control device and at the same time the reference light sensor measures at least one reference light intensity of emitted light towards the sample plane and transmits the at least one measured reference light intensity to the control device f) the control device corrects the at least one measured signal light intensity with the at least one reference light intensity and the calculated sensitivity of the reference light sensor.

The present disclosure also relates to a laboratory instrument comprising a detection unit and a control device. The detection unit comprises a light source, a sample plane comprising a sample holder configured to hold at least one sample vessel comprising a test sample to be illuminated, a reference light sensor, and a detector. The light source is configured to emit light towards the sample plane. The reference light sensor is located in proximity to the sample holder and configured to measure an initial light intensity of emitted light towards the sample plane and at least one reference light intensity of emitted light towards the sample plane. The detector is configured to measure a signal light intensity of emitted light from the sample plane. The control device is adapted to execute the steps of the method to correct signal light intensities measured by the detector of the detection unit in the laboratory instrument as described herein.

The disclosure further relates to a computer program product comprising instructions to cause the laboratory instrument as described herein to execute the steps of the method to correct signal light intensities measured by the detector of the detection unit in the laboratory instrument as described herein.

The present disclosure also relates to a computer-readable medium having stored thereon the computer program product comprising instructions to cause the laboratory instrument as described herein to execute the steps of the method to correct signal light intensities measured by the detector of the detection unit in the laboratory instrument as described herein.

DETAILED DESCRIPTION

Figure 1:
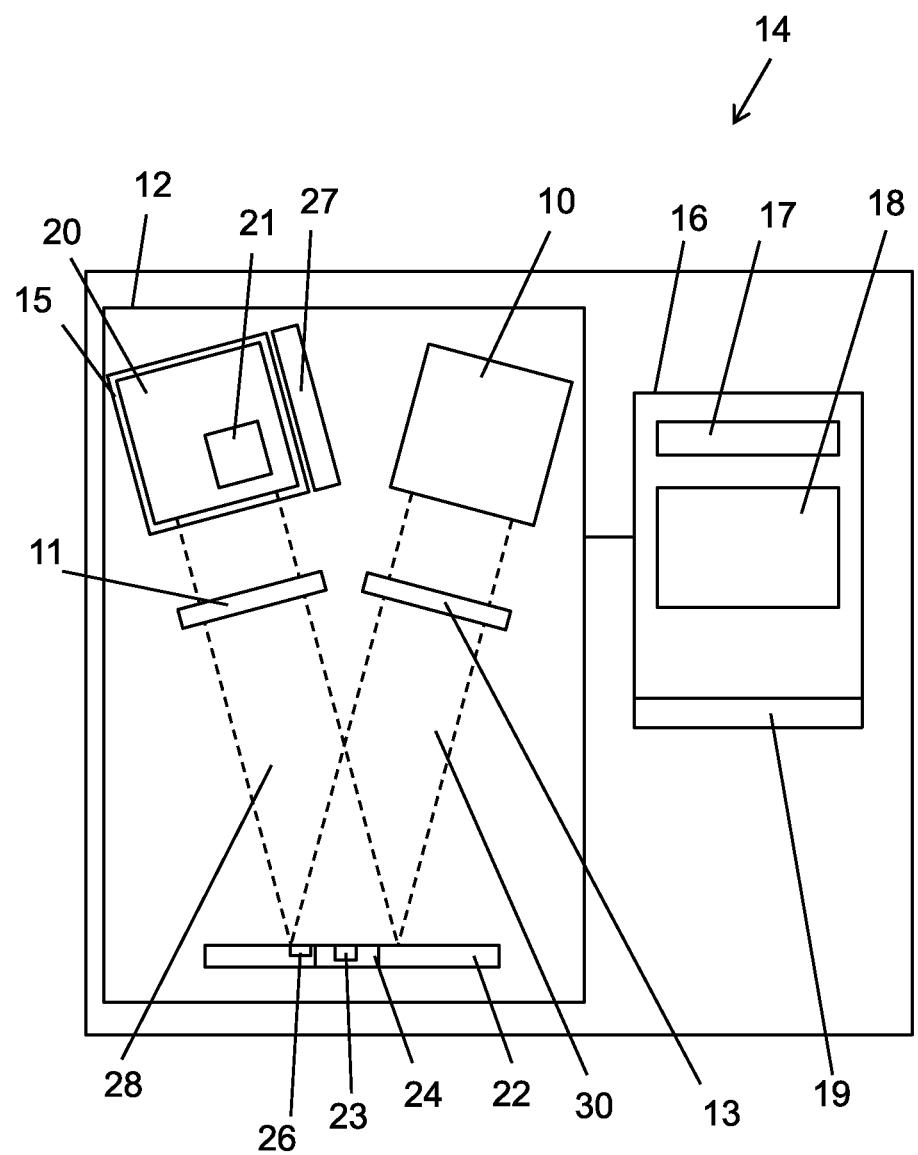
FIG. 1 shows an embodiment of a laboratory instrument.

The present disclosure relates to a method to correct signal light intensities measured by a detector of a detection unit in a laboratory instrument. The laboratory instrument comprises the detection unit and a control device. The detection unit comprises a light source, a sample plane comprising a sample holder configured to hold at least one sample vessel comprising a test sample to be illuminated, a reference light sensor, and the detector. The light source is configured to emit light towards the sample plane. The reference light sensor is located in proximity to the sample holder and configured to measure an initial light intensity of emitted light towards the sample plane and at least one reference light intensity of emitted light towards the sample plane. The detector is configured to measure a signal light intensity of emitted light from the sample plane. The method comprises the following steps:

a) the control device receives a basic light intensity of the light source
b) the control device activates the light source in the detection unit
c) the reference light sensor measures an initial light intensity of emitted light towards the sample plane and transmits the measured initial light intensity to the control device
d) the control device calculates a sensitivity of the reference light sensor based on the measured initial light intensity and the basic light intensity of the light source
e) the detector measures at least one signal light intensity of emitted light from the sample plane and transmits the at least one measured signal light intensity to the control device and at the same time the reference light sensor measures at least one reference light intensity of emitted light towards the sample plane and transmits the at least one measured reference light intensity to the control device
f) the control device corrects the at least one measured signal light intensity with the at least one reference light intensity and the calculated sensitivity of the reference light sensor.

As used herein, the term "laboratory instrument" relates to an analytical apparatus or device configured to conduct a laboratory test on a test sample. A laboratory instrument can be designed, for example, to use a test sample or part of the test sample in order to produce a measurable signal light, on the basis of which it is possible to determine whether an analyte of interest is present in the test sample, and if desired in what concentration. The laboratory instrument comprises a detection unit. As non-limiting examples the detection unit may be a photometer, a fluorometer, a turbidimeter, a nephelometer, a luminometer, a fluorescence polarimeter, a flame photometer, an atomic absorption photometer, a flow cytometer, or an imaging system for detecting and/or measuring an analyte-related signal light of the test sample.

The detection unit comprises a light source. The detection unit may further comprise a light source holder for mounting the light source so that the light source can emit light towards the sample plane. Thus, the light source is configured to emit light towards the sample plane so that a test sample may be illuminated. The emitted light towards the sample plane may interact with an analyte, analyte-related parameter, or analyte-related substance of a test sample resulting in measurable signal light whose intensity can be measured by the detector as further described below. As non-limiting examples the interaction between the emitted light and the analyte, analyte-related parameter, or analyte-related substance may be based on reflection, scattering, absorption including fluorescence, luminescence, refraction, optical activity, and photoelectric effect. As non-limiting examples the light source may be a light-emitting diode (LED), a halogen lamp, a xenon lamp, or a laser.

In a specific embodiment, the light source comprises at least one light-emitting diode (LED) mounted on a printed circuit board.

For the light source its basic light intensity may be determined. As used herein, the term "basic light intensity" relates to an absolute light intensity or power of emitted light from a newly manufactured light source at a nominal current and measured by a calibrated light sensor. The light source may comprise a basic light intensity within the scope of general manufacturing accuracies of the light source. As non-limiting examples the basic light intensity may be measured and expressed as optical power output (Watt) or irradiance (Watt per square meter). Furthermore, the basic light intensity may be represented by an arbitrary unit of the light intensity emitted from the light source. For example, the measured optical power output (Watt) or irradiance (Watt per square meter) may be converted and expressed in "counts" or any other numeric value using an analog-to-digital converter, wherein the counts or numeric values may represent either a power or an energy depending on the used calibrated light sensor.

The detection unit further comprises a sample plane comprising a sample holder configured to hold at least one sample vessel comprising a test sample to be illuminated. As used herein, the term "sample holder" relates to any device adapted for receiving, holding, and/or releasing at least one sample vessel containing a test sample and/or a test reagent. The sample holder may comprise at least one insertion area or recess configured to receive and accommodate one or more sample vessels in a manner that illumination of the one or more test samples as well as the detection of the resulting signal light emitted from the one or more test samples can be facilitated.

In one embodiment, the sample holder has a cylindrical shape, a closed bottom, and a top with an insertion area for inserting one sample vessel in an upright position. A non-limiting example of such a sample holder is a single sample vessel holder.

In one embodiment of the sample holder, the sample holder has a bottom comprising a hole, slit or a transparent area so that a part of the light emitted from the light source towards the sample plane may be absorbed by the analyte, analyte-related parameter, or analyte-related substance and the non-absorbed part of the light may pass through the hole, slit or a transparent area and subsequently detected by the detector.

In another embodiment of the sample holder, the sample holder has side walls comprising a hole, slit or a transparent area so that a part of the light emitted from the light source towards the sample plane may be absorbed by the analyte or analyte-related substance and the non-absorbed part of the light may pass through the hole, slit or a transparent area and subsequently detected by the detector.

In another embodiment, the sample holder has a cubic shape, a closed bottom, and a top with one or multiple insertion areas or recesses for inserting one or multiple sample vessels in an upright position. A non-limiting example of such a cubic test sample holder is a test sample block configured to receive, hold, and/or release one or multiple sample vessels or a multi-well plate.

As used herein, the term "sample vessel" relates to a container or receptacle adapted for receiving, storing, transporting, and/or releasing a content such as a test sample (e.g. blood, urine, serum, plasma, or liquefied biopsy sample, etc.), a test reagent (e.g. reagent for immunochemistry tests, clinical chemistry tests, coagulation tests, hematological tests, molecular biological tests, etc.), or a combination thereof. Depending on the content of the sample vessel, detection method, and manufacturer the material as well as the dimension of the sample vessel like diameter, side length, height and geometry varies.

In one embodiment, the sample vessel may be a vessel with a cylindrical, conical or cubic shape. The sample vessel may have a closed bottom and an open top. The closed bottom of the cylindrical vessel can be rounded and the open top may be closable, e.g. by using a cap. The side walls of the sample vessel may be made of a transparent material, e.g. transparent plastic or glass. A non-limiting example of a single cylindrical or conical sample vessel is a primary sample vessel or a measuring cuvette which are well known in the art. Alternatively, two or more sample vessels may be arranged as a multi sample vessel assembly. A non-limiting example of such a multi sample vessel assembly is a multi-well plate which is well known in the art.

As used herein, the term "test sample" relates to a patient's specimen (e.g. serum, plasma, whole blood, urine, stool, sputum, cerebrospinal fluid, bone marrow, etc.) from which the presence and if desired the concentration of an analyte or parameter of interest can be determined using a laboratory test. As a test sample is taken from an individual patient at a certain time, corresponding analytes or parameters of interest are unique for each test sample.

The detection unit further comprises a reference light sensor. The reference light sensor is located in proximity or adjacent to the sample holder of the detection unit. As the reference light sensor is in proximity to the sample holder, the reference sensor and the sample holder are exposed to the substantially same light emitted from the light source towards the sample plane. The light sensor may be mounted on or next to the sample plane so that the reference sensor does not interrupt with the emitted light towards the sample holder. Alternatively, the reference light sensor may be comprised by the sample plane or sample holder. For example, the sample plane or sample holder may comprise a recess in which the reference light sensor can be mounted. As non-limiting examples the reference light sensor may be a photodiode, a photoresistor, or a phototransistor.

In a specific embodiment, the reference light sensor comprises one or more photodiodes. And the reference light sensor is configured to measure an initial light intensity of emitted light towards the sample plane and at least one reference light intensity of emitted light towards the sample plane.

As used herein, the term "initial light intensity" relates to a relative light intensity of emitted light from a light source towards a sample plane and measured by an uncalibrated reference light sensor. The initial light intensity may be measured by the reference light sensor when the light source is activated in the detection unit of the laboratory instrument for the first time. Thus, the initial light intensity may relate to an intensity of emitted light from a newly manufactured light source and may be measured once before the laboratory instrument is put into operation where then reference light intensities and signal light intensities are measured for analyzing test samples. The measured initial light intensity and the basic light intensity of the light source are used to determine or calculate the sensitivity of the reference light sensor and thereby to calibrate the reference light sensor. As a non-limiting example the initial light intensity may be measured and expressed in "photocurrent (A)" if the reference light sensor is one or more photodiodes. Furthermore, the initial light intensity may be represented by an arbitrary unit of a light intensity emitted from the light source. For example, the measured photocurrent (A) may be converted and expressed in "counts" or any other numeric value using an analog-to-digital converter, wherein the counts or numeric values may represent either a power or energy depending on the used reference light sensor.

As used herein, the term "reference light intensity" relates to a light intensity of emitted light from the light source towards a sample plane and measured by the reference light sensor after measurement of the initial light intensity and calculation of its sensitivity. A reference light intensity may be measured when the detector measures a signal light intensity of emitted light from the sample plane. Thus, for each measured signal light intensity a corresponding reference light intensity may be measured. A reference light intensity may be measured when the light source is still activated after measurement of the initial light intensity or when the light source is reactivated after deactivating the light source. As the sensitivity of the reference light sensor is known when reference light intensities are measured, the reference light intensities can now be used to correct measured signal light intensities on the basis of which absolute or quantitative test results may be calculated. Thus, a reference light intensity and the calculated sensitivity of the corresponding reference light sensor are used to correct a corresponding signal light intensity measured by the detector. As a non-limiting example the reference light intensity may be measured and expressed in "photocurrent (A)" if the reference light sensor is one or more photodiodes. Furthermore, the initial light intensity may be represented by an arbitrary unit of a light intensity emitted from the light source. For example, the measured photocurrent (A) may be converted and expressed in "counts" or any other numeric value using an analog-to-digital converter, wherein the counts or numeric values may represent either a power or energy depending on the used reference light sensor.

The detection unit further comprises a detector. The detector is configured to measure a signal light intensity of emitted light from the sample plane. The detection unit may further comprise a detector holder for mounting the detector so that the light emitted from the sample plane can be detected and the signal light intensity can be measured. The detector may be calibrated so that measured signal light intensities can be used for calculating comparable quantitative test results. The detector may operate within a tight manufacturing tolerance for a high reproducibility of measured signal light intensities, e.g. measured signal light intensities of a certain signal light intensity may vary within a range smaller than +/−5%.

In a specific embodiment, the detector comprises a single photodiode, a charge-coupled device (CCD), or a complimentary metal-oxide semiconductor (CMOS) sensor.

As used herein, the term "signal light intensity" relates to a light intensity of emitted light from the sample plane comprising a sample holder configured to hold at least one sample vessel comprising a test sample to be illuminated. The signal light intensity may be measured by a calibrated detector. If the sample plane holds a test sample to be illuminated, the measured signal light intensity may be associated with an analyte, analyte-related parameter, or analyte-related substance of the test sample. The emitted light from the sample plane or at least a part of the emitted light from the sample plane may be emitted from the analyte, analyte-related parameter, or analyte-related substance of the test sample. The measured signal light intensity is then processed to a test result indicating the presence and/or the concentration of an analyte of interest in the test sample. The test result may be determined or calculated by multiple measured signal light intensities. For example, the test result may be based on a first signal light intensity measured when the light source was activated and a second signal light intensity measured when the light source was not activated. And the second signal light intensity may be subtracted from the first signal light intensity for calculating the test result.

If the sample plane doesn't hold a test sample to be illuminated, the measured signal light intensity may be associated with a background signal of the sample plane. The measured signal light intensity associated with the background signal of the sample plane may be subtracted from the measured signal light intensity or signal light intensities associated with an analyte, analyte-related parameter, or analyte-related parameter of the test sample for calculating the test result. As non-limiting examples the signal light intensity may be measured and expressed in "photocurrent (A)" if the detector is one or more photodiodes, a phot ASIC, or photomultiplier tube (PMT), in "electric potential (V)" if the detector is a complimentary metal-oxide semiconductor (CMOS), or in "electric charge (C)" or "photocurrent (A)" if the detector is a charge-coupled device (CCD). Furthermore, the signal light intensity may be represented by an arbitrary unit of the light intensity of emitted light from the sample plane. For example, the measured photocurrent (A) or electric potential (V) may be converted and expressed in "counts" or any other numeric value using an analog-to-digital converter, wherein the counts or numeric values may represent either a power or energy depending on the used detector.

In one embodiment, the light source is located above the sample plane and configured to emit light towards the sample holder of the sample plane from the top. The reference light sensor is located in close proximity to the sample holder. And the detector is located above the sample plane and configured to measure a signal light intensity of emitted light from the sample holder from the top. Such a configuration may be useful if the detection unit relates to an imaging system.

In another embodiment, the sample plane is located between the light source and the detector. The light source is configured to emit light towards the sample holder of the sample plane and the detector is configured to measure a signal light intensity of emitted light from the sample holder of the sample plane. And the reference light sensor is located in close proximity to the sample holder. In such a configuration, the bottom or the sidewalls of the sample holder may comprise a hole, slit or a transparent area so that a part of the light emitted from the light source towards the sample plane may be absorbed by the analyte, analyte-related parameter, or analyte-related substance and the non-absorbed part of the light may pass through the hole, slit or a transparent area and subsequently detected by the detector. Such a configuration may be useful if the detection unit relates to a photometer.

In another embodiment, the detection unit may comprise one or more excitation filters for selecting an excitation wavelength of the light emitted from the light source. For example, such excitation filters are well known in the area of fluorescence imaging or spectroscopic applications. The excitation filter may be short pass filters or band pass filter. Variations of these filters exist in the form of notch filters or deep blocking filters. Other forms of excitation filters include the use of monochromators, wedge prisms coupled with a narrow slit and the use of holographic diffraction gratings, etc. The excitation filter may be located between the light source and the sample plane in the beam of the light emitted from the light source towards the sample plane. The detection unit may further comprise an emission filter for selecting an emission wavelength of the light emitted from the sample plane.

In a further embodiment, the detection unit may comprise one or more optical lenses for focusing and/or dispersing light emitted from the light source towards the sample plane and/or light emitted from the sample plane towards to detector from the sample plane.

The laboratory instrument may further comprise, for example, at least one device from the group of following devices: a sorting device for sorting test samples or sample vessels, a cap removal device for removing caps or closures on sample vessels, a cap fitting device for fitting caps or closures on sample vessels, a cap removal/fitting device for removing/fitting caps or closures on sample vessels, a pipetting device for pipetting a test sample and/or test reagent, an aliquoting device for aliquoting test samples and/or test reagents, a centrifuging device for centrifuging test samples and/or test reagents, a heating device for heating a test sample and/or test reagent, a cooling device for cooling a test sample and/or test reagent, a mixing device for mixing a test sample and/or test reagent, an isolation device for isolating an analyte of the test sample, a storing device for storing test samples and/or test reagents, an archiving device for archiving test samples and/or test reagents, a sample vessel type determination device for determining a sample vessel type, a test sample quality determination device for determining a test sample quality, a sample vessel identification device for identifying a sample vessel. Such devices of a laboratory instrument are well known in the art.

The laboratory instrument further comprises a control device. The term "control device" as used herein encompasses any physical or virtual processing device comprising a processor which is configured to control the laboratory instrument in a way that test sample processing steps and test sample analysis steps are conducted by the laboratory instrument. The control device may receive information from a data management unit regarding which steps need to be performed with a certain test sample. The processor of the control device may, for instance, be embodied as a programmable logic controller adapted to execute a computer-readable program provided with instructions to perform operations of the laboratory instrument. One operation is to control the detection unit of the laboratory instrument to measure an initial light intensity, signal light intensities, and corresponding reference light intensities. Another operation is to conduct a method for correcting signal light intensities measured by the detector of a detection unit in the laboratory instrument as described herein.

In one embodiment of the method, the basic light intensity of the light source is measured by a calibrated light sensor of a light source test-system and the light source test-system is separate from the laboratory instrument. And in step a) of the method the control device receives the basic light intensity of the light source when the light source is mounted in the detection unit for the first time.

As used herein, the term "light source test-system" relates to a system for measuring a basic light intensity of a newly manufactured light source before the light source is mounted in the detection unit of the laboratory instrument which is spatially separated from the light source test-system. The light source test-system comprises a calibrated light sensor for determining the absolute basic light intensity of the new light source which may be expressed as optical power output (Watt) or irradiance (Watt per square meter). Such calibrated light sensors are well known in the art. As a non-limiting example the calibrated light sensor may be a photodiode or photodiodes which are calibrated on a regular basis by an operator of the light source test-system. The light source test-system may further comprise a test unit and a further control device. The test unit may comprise a further light source holder for mounting the light source to be tested and a measuring plane comprising the calibrated light sensor. After mounting the light source in the test unit the light source is configured to emit light towards the measuring plane comprising the calibrated light sensor. The calibrated light sensor measures the basic light intensity of emitted light towards the measuring plane after activating the light source for the very first time after manufacturing. The measured basic light intensity may then be transmitted to the further control device of the light source test-system and stored in a memory of the further control device.

There are multiple and different ways how the control device of the laboratory instrument can receive the basic light intensity from the light source test-system when the light source is mounted in the detection unit of the laboratory instrument for the first time.

In one embodiment of the method, in step a) the control device receives the basic light intensity from the light source test-system by transmitting the basic light intensity from the light source test-system to the control device or by reading out the basic light intensity of the light source from a memory mounted on the light source after the basic light intensity of the light source was stored on said memory by the light source test-system.

In one embodiment, the control device of the laboratory instrument and the further control device of the light source test-system may be communicatively connected to each other. For example, the basic light intensity may be transmitted from the light source test-system to the laboratory instrument via an internet based data transmission channel. The light source test-system may be connected to multiple laboratory instruments in order to provide corresponding basic light intensities worldwide. Furthermore, the transmitted basic light intensity may be associated with a specific serial number or other unique identification means of the light source so that the correct basic light intensity can be assigned to a certain light source mounted in the laboratory instrument.

In another embodiment, the light source test-system may further comprise a programming or writing device connected to the further control device and configured to store the basic light intensity on a memory mounted on the light source. And the laboratory instrument may further comprise a reading device connected to the control device and configured to read out the basic light intensity stored on the memory mounted on the light source. When the light source is mounted in the detection unit of the laboratory instrument for the first time the reading device connected to the control device is reading out the basic light intensity of the light source from the memory mounted on the light source.

In a more specific embodiment, the light source comprises at least one light-emitting diode mounted on a printed circuit board and the memory is an electrically erasable programmable read-only memory (EEPROM) mounted on the printed circuit board. The basic light intensity is stored on the EEPROM using an EEPROM writing device or programming device connected to the further control device of the light source test-system and read out by an EEPROM reading device connected to the control device of the laboratory instrument.

In another specific embodiment, the memory may be a radio-frequency identification tag (RFID tag) mounted on the light source. The basic light intensity is stored on the RFID tag using a RFID writing device connected to the further control device of the light source test-system and read out by a RFID reading device connected to the control device of the laboratory instrument.

In one embodiment, the further control device of the light source test-system may comprise a further user interface configured to display the measured basic light intensity. The displayed basic light intensity can be noted/printed and then entered manually at the user interface of the control device of the laboratory instrument by a service technician. Alternatively, the basic light intensity can be stored on a mobile memory device which is compatible with the further control device and the control device. And the mobile memory device can be transported from the light source test-system to the laboratory instrument.

In one embodiment, the timing of step a) of the method may be independent of the timing of the step sequence comprising step b) and c). Step a) may be executed before, after, or at the same time of the step sequence comprising step b) and c). Thus, the control device may receive the basic light intensity from the light source test-system before, after, or at the same time when the light source is activated or turned on in the detection unit for the first time and the initial light sensitivity is measured by the reference light sensor. For example, the light source may be mounted in a light source holder of the detection unit of the laboratory instrument. Then, the basic light intensity is read out from the memory mounted on the light source. Subsequently, the light source is activated or turned on for the first time in the detection unit of the laboratory instrument and the reference light sensor measures the initial light intensity. In another example, the light source may be mounted in a light source holder of the detection unit of the laboratory instrument. Then, the light source is activated or turned on for the first time in the detection unit of the laboratory instrument and the reference light sensor measures the initial light intensity. And at the same time the basic light intensity is transmitted from the further control device of the light source test-system to the control device of the laboratory instrument via an internet based data transmission channel. The control device needs to receive the basic light intensity and the measured initial light intensity before step d) so that the sensitivity of the reference light sensor can be calculated.

In one embodiment, the sensitivity of the reference light sensor is the measured initial light intensity divided by the basic light intensity of the light source:

$$\text{sensitivity of reference light sensor} = \frac{\text{initial light intensity}}{\text{basic light intensity}}$$

Thus, by linking a measured relative light intensity (initial light intensity) with a measured absolute light sensitivity (basic light intensity) the sensitivity of the reference light sensor is determined and subsequent measurements of reference light intensities by the reference light sensor with consideration of its sensitivity can be used for correcting measured signal light intensities on the basis of which absolute or quantitative comparable test results can be calculated. As soon as the sensitivity of the reference light sensor is calculated or determined it may be stored on a memory of the control device and the light source may be deactivated.

After determining the sensitivity of the reference sensor, sample vessels comprising a test sample may be inserted into the sample holder of the sample plane and the light source may be activated again. Signal light intensities of emitted light from the sample plane measured by the detector of the detection unit and corresponding reference light intensities measured by the reference light sensor may be acquired simultaneously and transmitted to the control device. Based on the measured reference light intensity and the calculated sensitivity of the reference light sensor a measured signal light intensity can be corrected. In one embodiment, the corrected signal light intensity is the measured signal light intensity divided by the corresponding measured reference light intensity and multiplied by the calculated sensitivity of the reference light sensor:

$$\text{Corrected signal light intensity} = \text{signal light intensity} \cdot \frac{\text{sensitivity of reference light sensor}}{\text{reference light intensity}}$$

wherein $$\text{sensitivity of reference light sensor} = \frac{\text{initial light itensity}}{\text{basic light instensity}}$$

The corrected signal light intensity can now be used to calculate quantitative test results which are comparable to quantitative test results derived from corrected signal light intensities of other laboratory instruments of the same type.

In one embodiment, the corrected signal light intensity may further be multiplied by a scaling factor so that the corrected signal light intensity is human readable or better comparable to the measured signal light intensity:

$$\text{Corrected signal light intensity} = \text{signal light intensity} \cdot \frac{\text{sensitivity of reference light sensor}}{\text{reference light intensity}} \cdot \text{scaling factor}$$

This may be advantageous if the calibrated light sensor, the reference light sensor, and the detector measure the basic light intensity, the initial light intensity, the reference light intensities, and the signal light intensities in different units and/or measuring scales.

EXAMPLE

Measuring scale of calibrated light sensor of the light source test-system: 1-500 mW
Measured basic light intensity: 450 mW
Measuring scale of reference light sensor of the laboratory instrument: 1-65535 counts
Measured initial light intensity: 19500 counts
Measured reference light intensity: 19000 counts
Measuring scale of detector of the laboratory instrument: 1-300 mW
Measured signal light intensity: 200 mW
Scale factor: 500 mW Based on the above-mentioned basic light intensity, initial light intensity, reference light intensity, signal light intensity, and scale factor the corrected signal light intensity can be calculated as follows:

$$\text{Corrected signal light intensity} = 200 \text{ mW} \cdot \frac{\frac{19500 \text{ counts}}{450 \text{ mW}}}{19000 \text{ counts}} \cdot 500 \text{ mW} = 228.07 \text{ mW}$$

The corrected signal light intensity can now easily be compared to the measured signal light intensity. Furthermore, the differences between measured signal light intensity and corrected light intensities may be plotted over time in order to monitor the light source. Such information may be used to initiate maintenance activities. For example, if the difference between the measured signal light intensity and corrected light intensities exceeds a predefined threshold the exchange or maintenance of the light source may be triggered.

In one embodiment, the basic light intensity is associated with a basic light intensity minimum acceptance value. As used herein, the term "basic light intensity minimum acceptance value" relates to a predefined threshold value for monitoring the operation of the light source. As long as this threshold value is not undercut, the light source emits enough light towards the sample plane for generating signal light intensities on which reliable test results can be calculated. The basic light intensity minimum acceptance value may be defined after measuring the basic light intensity of a newly manufactured light source in the light source test-system. For each newly manufactured light source its corresponding basic light intensity minimum acceptance value may be determined. Thus, the basic light intensity minimum acceptance value may depend on the measured basic light intensity.

In a further embodiment, the control device receives the basic light intensity minimum acceptance value in step a) of the method and calculates at least one comparison value based on the at least one measured reference light intensity and the sensitivity of the reference light sensor. Then, the control device compares the basic light intensity minimum acceptance value with the at least one comparison value. The control device further comprises a user interface. If the at least one comparison value is smaller than the basic light intensity minimum acceptance value a warning message, an error message, or a user notification indicating that the light source needs to be exchanged is displayed on the user interface. The warning message may comprise a notification or indication like a test result flag indicating that with the currently mounted light source no reliable test results can be calculated. The error message may comprise a notification indicating that with the currently mounted light source no reliable signal light intensities can be measured and therefore the light source has been automatically deactivated in order to prevent further signal light intensity measurements. The user notification may indicate that the light source needs to be exchanged and may comprise additional information such as the light source identity (e.g. serial number), time in operation, number of executed laboratory tests, basic light intensity, basic light intensity minimum acceptance value, initial light intensity, sensitivity of corresponding reference sensor, last measured reference light intensity or intensities, and instructions for exchanging the light source.

In one embodiment, the basic light intensity minimum acceptance value and the basic light intensity may be transferred together or independent from each other from the light source test-system to the control device of the laboratory instrument. For example, the control device may receive the basic light intensity minimum acceptance value from the light source test-system by transmitting the basic light intensity minimum acceptance value from the light source test-system to the control device or by reading out the basic light intensity minimum acceptance value of the light source from a memory mounted on the light source after the basic light intensity minimum acceptance value of the light source was stored on said memory by the light source test-system.

In one embodiment, the basic light intensity minimum acceptance value may be transmitted from the light source test-system to the laboratory instrument via an internet based data transmission channel. The light source test-system may be connected to multiple laboratory instruments in order to provide corresponding basic light intensity minimum acceptance values worldwide. Additionally, the transmitted basic light intensity minimum acceptance value may be associated with a specific serial number or other unique identification means of the light source so that the correct basic light intensity minimum acceptance value can be assigned to a certain light source mounted in a laboratory instrument.

In another embodiment, the basic light intensity minimum acceptance value is stored on the memory mounted on the light source and the control device receives the basic light intensity minimum acceptance value by reading out the basic light intensity minimum acceptance value from the memory mounted on the light source. The light source test-system may further comprise a programming or writing device connected to the further control device and configured to store the basic light intensity minimum acceptance value on the memory mounted on the light source. The laboratory instrument may further comprise a reading device connected to the further control device and configured to read out the basic light intensity minimum acceptance value stored in the memory mounted on the light source. When the light source is mounted in the detection unit the reading device connected to the control device may read out the basic light intensity minimum acceptance value of the light source from a memory mounted on the light source.

In a more specific embodiment, the light source comprises at least one light-emitting diode mounted on a printed circuit board and the memory is an electrically erasable programmable read-only memory (EEPROM) mounted on the printed circuit board. The basic light intensity minimum acceptance value may be stored on the EEPROM using an EEPROM writing device or programming device connected to the further control device of the light source test-system and read out by an EEPROM reading device connected to the control device of the laboratory instrument.

In another specific embodiment, the memory is a radio-frequency identification tag (RFID tag) mounted on the light source. The basic light intensity minimum acceptance value is stored on the RFID tag using a RFID writer connected to the further control device of the light source test-system and read out by a RFID reader connected to the control device of the laboratory instrument.

In an alternative embodiment, the basic light intensity minimum acceptance value may be entered manually at the user interface of the control device of the laboratory instrument by a service technician. Alternatively, the basic light intensity minimum acceptance value can be stored on a mobile memory device which is compatible with the further control device and the control device. And the mobile memory device can be transported from the light source test-system to the laboratory instrument.

In a further embodiment, a further memory is mounted on the light source and the basic light intensity minimum acceptance value is stored on the further memory mounted on the light source and the control device receives the basic light intensity minimum acceptance value by reading out the basic light intensity minimum acceptance value from the further memory mounted on the light source.

As used herein, the term "comparison value" relates to a calculated actual intensity of the light source for monitoring the operation of the light source. As long as this comparison value is above the basic light intensity minimum acceptance of light source, the light source emits enough light towards the sample plane for generating signal light intensities on which reliable test results can be calculated.

In one embodiment, the at least one comparison value is the at least one measured reference light intensity divided by the sensitivity of the reference light sensor:

$$\text{comparison value} = \frac{\text{reference light intensity}}{\text{sensitivity of reference sensor}}$$

wherein $$\text{sensitivity of reference light sensor} = \frac{\text{initial light itensity}}{\text{basic light instensity}}$$

For monitoring the operation of the light source the control device calculates a comparison value on a regular basis (e.g. after a predefined time duration, after a predefined number of reference light intensity measurements, or after a predefined number of executed laboratory tests) and compares the basic light intensity minimum acceptance value with the calculated comparison value. A comparison value which is smaller than the basic light intensity minimum acceptance value indicates that the light source does not emit enough light towards the sample plane for generating signal light intensities on which reliable test results can be calculated. The light source needs to be maintained or exchanged and a warning message, an error message, or a user notification indicating that the light source needs to be exchanged is displayed on the user interface of the control device of the laboratory instrument.

Example

Measured basic light intensity: 450 mW
Basic light intensity minimum acceptance value: 400 mW
Measured initial light intensity: 19500 counts
Measured reference light intensity: 16000 counts
Based on the above-mentioned basic light intensity, initial light intensity, and reference light intensity, the comparison value can be calculated as follows:

$$\text{comparison value} = \frac{16000 \text{ counts}}{\frac{19500 \text{ counts}}{450 \text{ mW}}} = 369.2 \text{ mW}$$

As the calculated comparison value (369.2 mW) is smaller than the basic light intensity minimum acceptance value (450 mW) the light source needs to be maintained or exchanged. Thus, the operation of the light source may also be monitored without measured signal light intensities as described above.

In one embodiment, the detection unit comprises at least one excitation filter which is located between the light source and the light reference sensor and the light source test-system comprises at least one equal excitation filter which is located between the light source and the calibrated light sensor of the light source test-system. And for each excitation filter steps a) to f) of the method are conducted.

Depending on the application of the detection unit of the laboratory instrument, the detection unit may comprise one or more excitation filters for selecting an excitation wavelength of the light emitted from the light source towards the sample plane. As the basic light intensity, the initial light intensity, the reference light intensities, and the signal light intensities depend on the used excitation filters, the method to correct signal light intensities measured by a detector of a detection unit in a laboratory instrument needs to be carried out for each excitation filter in order to produce reliable test results. Accordingly, the light-source test system comprises equal excitation filters and measures the basic light intensity for each equal excitation filter using the same nominal current per excitation filter as used in the detection unit of the laboratory instrument, wherein an equal excitation filter of the light-source test system corresponds to an excitation filter of the same type also present in the detection unit of the laboratory instrument.

As the basic light intensity, the initial light intensity, the reference light intensities, and the signal light intensities may also depend on the used optical lenses (e.g. lenses with treated surfaces), the method to correct signal light intensities measured by a detector of a detection unit in a laboratory instrument needs to be carried out for each optical lens used in the laboratory instrument in order to produce reliable signal light intensities. Accordingly, the light-source test system comprises equal optical lenses and measures the basic light intensity for each equal optical lens, wherein an equal optical lens of the light-source test system corresponds to an optical lens of the same type also present in the detection unit of the laboratory instrument.

In a more specific embodiment, the laboratory instrument is configured to conduct a nucleic acid amplification reaction and at least one sample vessel comprising a test sample is inserted into the sample holder of the sample plane. The signal light intensity emitted from the sample plane during the nucleic acid amplification reaction is measured by the detector and used to determine the presence and the concentration of an analyte of interest in the test sample.

As used herein, the term "nucleic acid amplification reaction" relates to a method or reaction used in molecular biology to amplify a single copy or a few copies of a target DNA segment (analyte) to a detectable amount of copies of the DNA segment involving repeated cycles of temperature-dependent reactions with a polymerase. Each cycle may comprise at least a denaturation phase (e.g. 95° C. for 30 seconds), an annealing phase (e.g. 65° C. for 30 seconds), and an extension phase (e.g. 72° C. for 2 minutes). The sample holder may be in thermal contact with a thermoelectric element for heating and/or cooling the sample holder to predefined temperatures of the different phases. Typically, a nucleic acid amplification reaction consists of 20-40 repeated cycles and after each cycle the signal light intensity of the light emitted from the sample plane may be measured by the detector of the detection unit. Based on the measured signal light intensities the quantity of the DNA segment can be calculated. Alternatively, the signal light intensity of the light emitted from the sample plane is measured by the detector after the nucleic acid amplification reaction is completed. Based on the measured signal light intensity the presence of the target DNA segment can be determined. Laboratory instruments for conducting such nucleic acid amplification reactions are typically called thermocycler instruments and are well known in the art.

The present disclosure also relates to a laboratory instrument comprising a detection unit and a control device. The detection unit comprises a light source, a sample plane comprising a sample holder configured to hold at least one sample vessel comprising a test sample to be illuminated, a reference light sensor, and a detector. The light source is configured to emit light towards the sample plane. The reference light sensor is located in proximity to the sample holder and configured to measure an initial light intensity of emitted light towards the sample plane and at least one reference light intensity of emitted light towards the sample plane. The detector is configured to measure a signal light intensity of emitted light from the sample plane. The control device is adapted to execute the steps of the method to correct signal light intensities measured by the detector of the detection unit in the laboratory instrument as described herein.

The disclosure further relates to a computer program product comprising instructions to cause the laboratory instrument as described herein to execute the steps of the method to correct signal light intensities measured by the detector of the detection unit in the laboratory instrument as described herein.

The present disclosure also relates to a computer-readable medium having stored thereon the computer program product comprising instructions to cause the laboratory instrument as described herein to execute the steps of the method to correct signal light intensities measured by the detector of the detection unit in the laboratory instrument as described herein.

EXAMPLES

FIG. 1 shows a schematic representation of a laboratory instrument (14). The laboratory instrument (14) comprises a detection unit (12) and a control device (16). The detection unit (12) comprises a light source (20), a sample plane (22) comprising a sample holder (24) configured to hold at least one sample vessel (23) comprising a test sample to be illuminated, a reference light sensor (26), and a detector (10). As shown in FIG. 1 the light source (20) may be mounted in a light source holder (15) above the sample plane (22) and configured to emit light (28) towards the sample plane (22) from the top. The reference light sensor (26) is located in close proximity to the sample holder (24). For example, the sample plane (22) comprises a recess in which the reference light sensor (26) can be mounted adjacent to the sample holder (24) as depicted in FIG. 1. Accordingly, the reference sensor (26) and the sample holder (24) are exposed to the substantially same light (28) emitted from the light source (20) towards the sample plane (22). After mounting the light source (20) in the detection unit (12) and activation of the light source (20) for the first time, the light reference sensor (26) is configured to measure an initial light intensity of emitted light (28) towards the sample plane (22). After measurement of the initial light intensity, the reference light sensor (26) is configured to measure at least one reference light intensity of emitted light (28) towards the sample plane (22) when the detector (10) is measuring a signal light intensity of emitted light (30) from the sample plane (22) during operation of the laboratory instrument (14). In the shown embodiment, the detector (10) is located above the sample plane (22) and configured to measure a signal light intensity of emitted light (30) from the sample plane (22) from the top. The shown detection unit (12) comprises an excitation filter (11) located between the light source (20) and the sample plane (22) in the beam of the light (28) emitted from the light source (20) towards the sample plane (22). The detection unit (12) further comprises an emission filter (13) located between the sample plane (22) and the detector (10) in the beam of the light (30) emitted from the sample plane (22) towards the detector (10). The detection unit may further comprise optical lenses (not shown) for focusing, directing and/or dispersing light emitted from the light source towards the sample plane for an optimal illumination of the at least one sample vessel (23) and/or for focusing, directing and/or dispersing light emitted from the sample plane towards to detector for an optimal measuring of the signal light intensity. The control device (16) comprises a processor (17) and a computer-readable medium (18) having stored thereon a computer program product comprising instructions to cause the control device (16) of the laboratory instrument (14) to execute the steps (44, 46, 48, 50, 52, 54) of the method (42) as further described in FIG. 4. The control device (16) may further comprise a user interface (19) on which a user notification such as a warning message, an error message, or a user notification indicating that the light source needs to be exchanged can be displayed in case the light source (20) needs to be maintained or exchanged. As further shown in FIG. 1, a memory (21) is mounted on the light source (20). The basic light intensity of the light source (20) as well as the basic light intensity minimum acceptance value of the light source (20) may be stored on the memory (21) which can be read out by a reading device (27) and transmitted to the control device (16) of the laboratory instrument (14).

Figure 2:
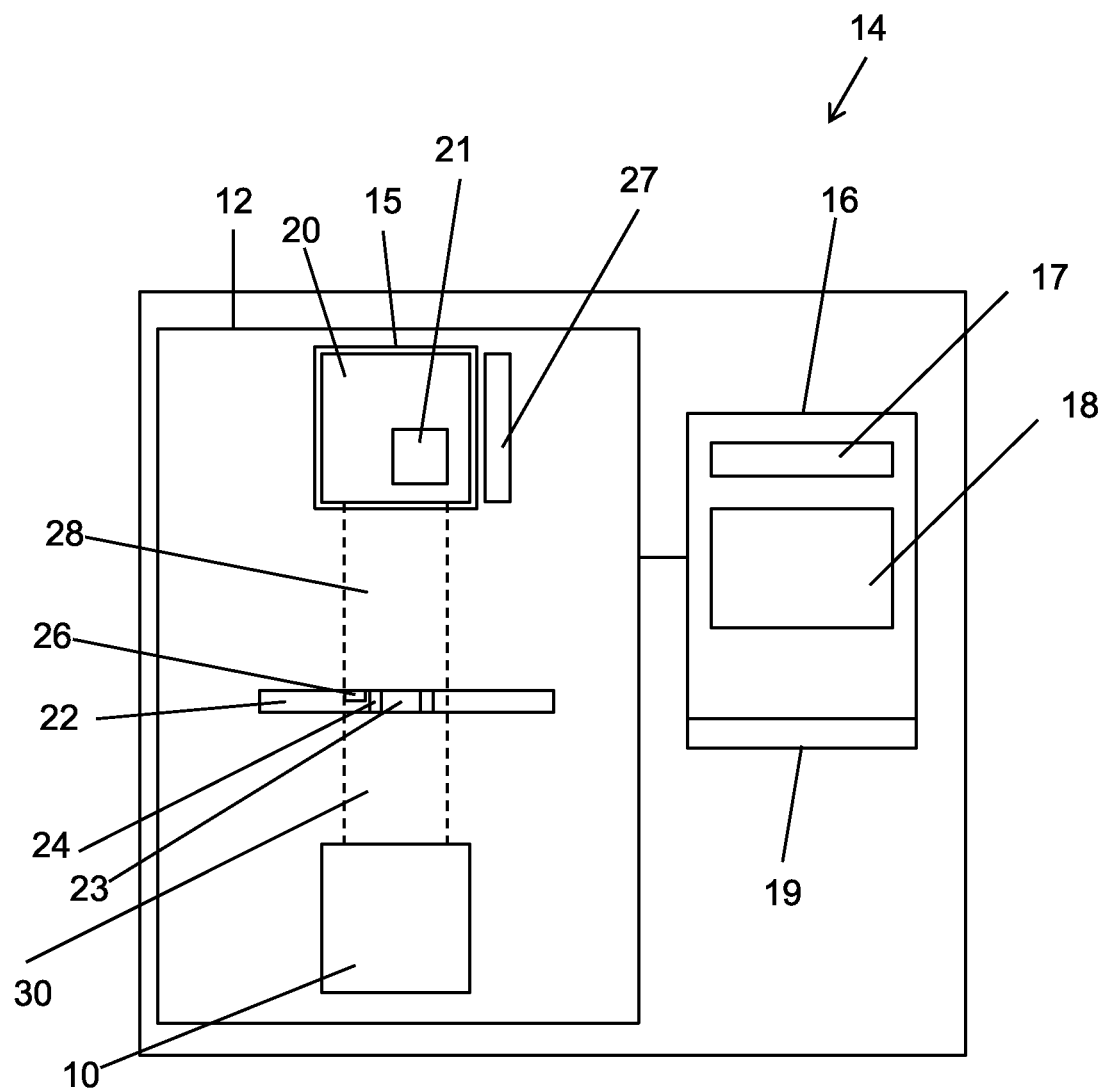
FIG. 2 depicts another embodiment of a laboratory instrument.

FIG. 2 depicts another embodiment of a laboratory instrument (14). The shown laboratory instrument (14) comprises a detection unit (12) and a control device (16). The detection unit (12) comprises a light source (20), a sample plane (22) comprising a sample holder (24) configured to hold at least one sample vessel (23) comprising a test sample to be illuminated, a reference light sensor (26), and a detector (10). In the shown embodiment, the sample plane (22) is located between the light source (20) and the detector (10). The light source (20) is mounted in a light source holder (15) configured to emit light (28) towards the sample holder (24) of the sample plane (22). The detector (10) is configured to measure a signal light intensity of emitted light (30) from the sample holder (23) of the sample plane (22). And the reference light sensor (26) is located in close proximity to the sample holder (24). For example, the sample plane (22) comprises a recess in which the reference light sensor (26) can be mounted adjacent to the sample holder (24). Accordingly, the reference sensor (26) and the sample holder (24) are exposed to the substantially same light (28) emitted from the light source (20) towards the sample plane (22). The bottom or the sidewalls of the sample holder (24) may comprise a hole, slit or a transparent area (not shown) so that a part of the light (28) emitted from the light source (20) towards the sample plane (22) may be absorbed by an analyte, analyte-related parameter, or analyte-related substance of the test sample in the test vessel (23). The non-absorbed part of the light (30) may be emitted from the sample plane (22) towards the detector (10) by passing through the hole, slit or a transparent area of the sample holder (24). After mounting the light source (20) in the detection unit (12) and activation of the light source (20) for the first time, the reference light sensor (26) is configured to measure an initial light intensity of emitted light (28) towards the sample plane (22). After measurement of the initial light intensity, the reference light sensor (26) is configured to measure at least one reference light intensity of emitted light (28) towards the sample plane (22) when the detector (10) is measuring a signal light intensity of emitted light (30) from the sample plane (22) during operation of the laboratory instrument (14). The control device (16) of the laboratory instrument (14) comprises a processor (17) and a computer-readable medium (18) having stored thereon a computer program product comprising instructions to cause the control device (16) of the laboratory instrument (10) to execute the steps (44, 46, 48, 50, 52, 54) of the method (42) as further described in FIG. 4. The control device (16) may further comprise a user interface (19) on which a user notification such as a warning message, an error message, or a user notification indicating that the light source needs to be exchanged can be displayed. As further shown in FIG. 2, a memory (21) is mounted on the light source (20). The basic light intensity of the light source (20) as well as the basic light intensity minimum acceptance value of the light source (20) may be stored on the memory (21) which can be read out by a reading device (27) and transmitted to the control device (16) of the laboratory instrument (14).

Figure 3:
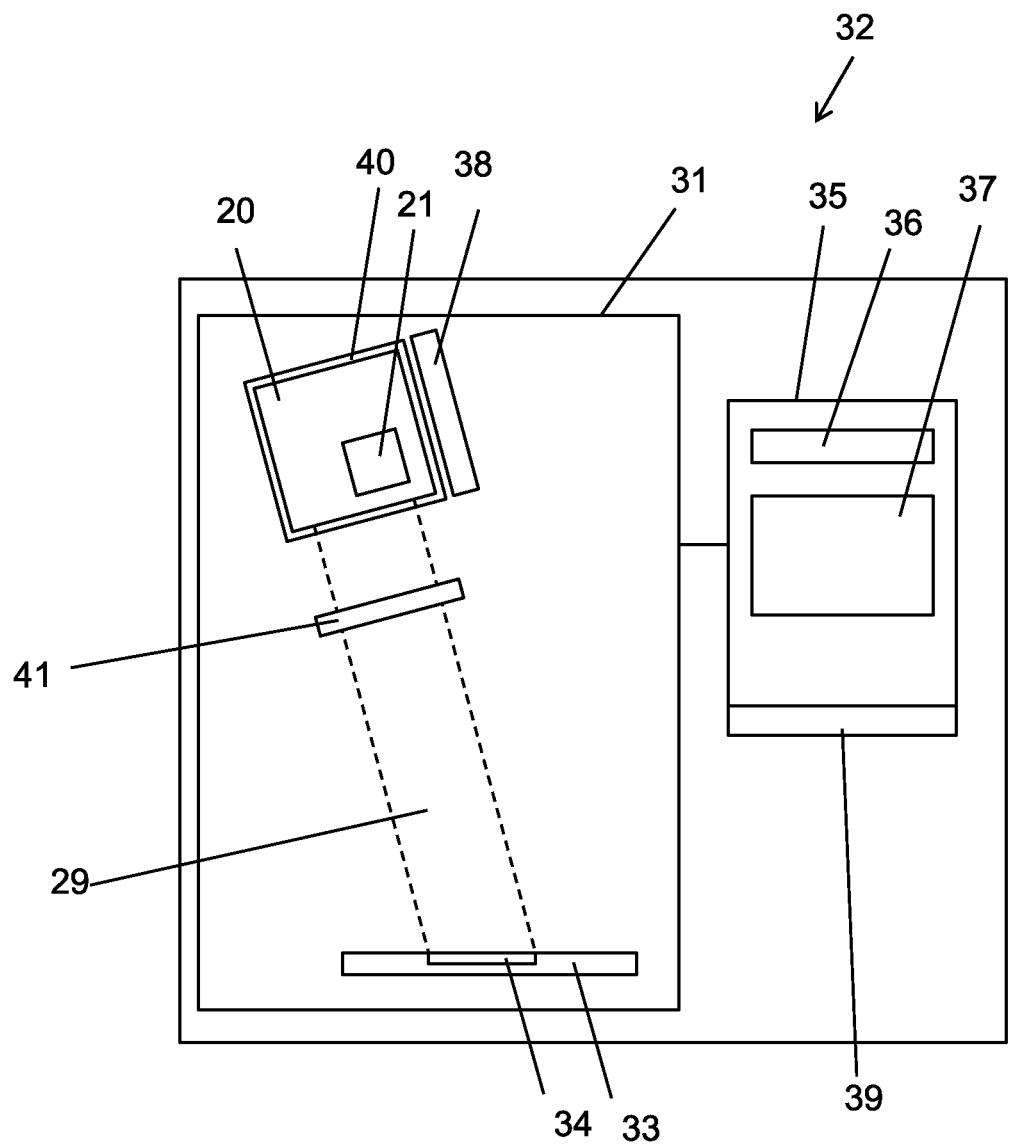
FIG. 3 shows an embodiment of a light-source test system.

In FIG. 3 a schematic representation of a light source test-system (32) is shown. The light source test-system (32) may comprise a test unit (31) and a further control device (35). The test unit (31) may comprise a further light source holder (40) for mounting the light source (20) and a measuring plane (33) comprising a calibrated light sensor (34). After mounting the light source (20) in the further light source holder (40) of the test unit (31), the light source (20) is configured to emit light (29) towards the measuring plane (33) comprising the calibrated light sensor (34), wherein the calibrated light sensor (34) measures a basic light intensity of emitted light (29) of the light source (20) towards the measuring plane (33). The measured basic light intensity is then transmitted to the further control device (35) of the light source test-system (32) and stored in a memory of the further control device (35). The setup of the further light source holder (40) and the measuring plane (33) of the test unit (31) as shown in FIG. 3 is substantially the same compared to the setup of the light source holder (15) and the sample plane (22) of the detection unit (12) of the laboratory instrument (14) as shown in FIG. 1. For example, the distance between the further light source holder (40) and the measuring plane (33) of the test unit (31) and the distance between the light source holder (15) and the sample plane (22) of the detection unit (12) are the same. Also the angle of incidence of the emitted light (29) towards the measuring plane (33) of the test unit (31) and the entrance angle of the emitted light (28) towards the sample plane (22) of the detection unit (12) are the same. Furthermore, the test unit (31) may comprise an equal excitation filter (41) which corresponds to an excitation filter present in the detection unit of the laboratory instrument. Thus, the excitation filter (11) of the detection unit (12) as shown in FIG. 1 and the equal excitation filter (41) of the test unit (31) are of the same type. And the calibrated light sensor (34) measures the basic light intensity after the emitted light (29) passed the equal excitation filter (41). The further control device (35) comprises a further processor (36) and a further computer-readable medium (37) having stored thereon a computer program product comprising instructions to measure, receive, store, transmit, or display the measured basic light intensity of the light source (20). The control device (16) may further comprise a further user interface (39) on which the measured basic light intensity can be displayed. As shown in FIG. 3, the light-source test system (32) may comprise a programming or writing device (38) connected to the further control device (35) and configured to store the basic light intensity and/or the basic light intensity minimum acceptance value on the memory (21) mounted on the light source (20).

Figure 4:
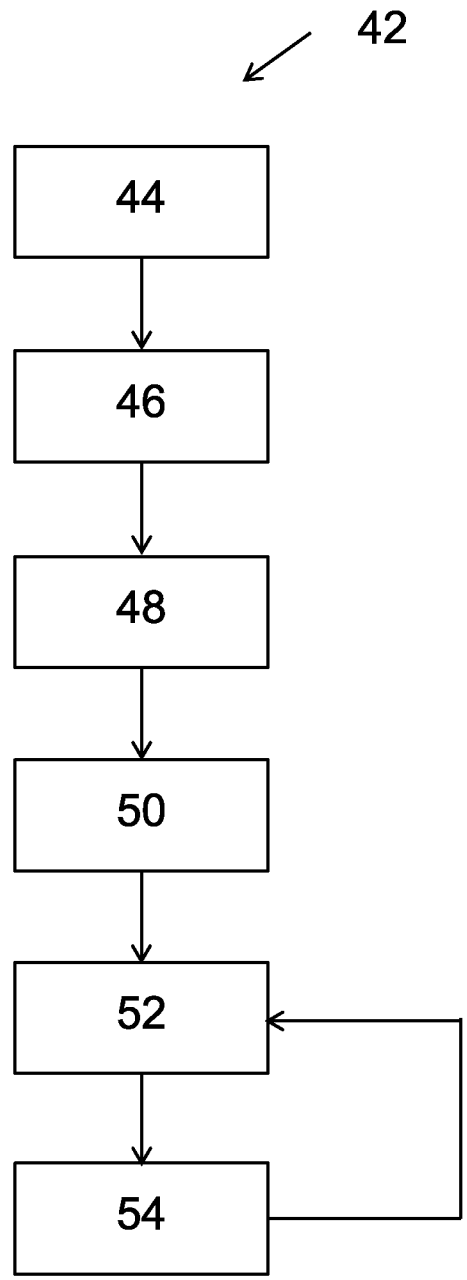
FIG. 4 depicts a flowchart of an embodiment of the method for correcting signal light intensities measured by a detector of a detection unit in a laboratory instrument.

FIG. 4 depicts a flowchart of an embodiment of the method (42) for correcting signal light intensities measured by a detector (10) of a detection unit (12) in a laboratory instrument (14). As shown in FIG. 4, the control device (16) of the laboratory instrument (10) receives a basic light intensity of the light source (20) in step a) (44) of the method as further described in FIG. 5 below. Then, the control device (16) activates the light source (20) in the detection unit (12) in step b) (46) of the method. In step c) (48) of the method, the reference light sensor (26) measures an initial light intensity of emitted light (28) towards the sample plane (22) and transmits the measured initial light intensity to the control device (16). Subsequently, the control device (16) calculates a sensitivity of the reference light sensor (26) based on the measured initial light intensity and the basic light intensity of the light source (20) in step d) (50). The calculated sensitivity may be stored on the control device (16). By calculating or determining the sensitivity of the reference light sensor (26) the reference light sensor (26) is now calibrated. In step e) (52) of the method, the detector (10) measures at least one signal light intensity of emitted light (30) from the sample plane (22) and transmits the at least one measured signal light intensity to the control device (16). At the same time the reference light sensor (26) measures at least one reference light intensity of emitted light (28) towards the sample plane (22) and transmits the at least one measured reference light intensity to the control device (16). Then, the control device (16) corrects the at least one measured signal light intensity with the at least one reference light intensity and the calculated sensitivity of the reference light sensor (26) in step f) (54) of the method. Once the sensitivity of the reference light sensor (26) is calculated or determined in step d) (50), step e) (52) to step f) (54) may be repeated for measuring and correcting signal light intensities associated with analytes, analyte-related parameters, or analyte-related substances of further test samples.

Figure 5A:
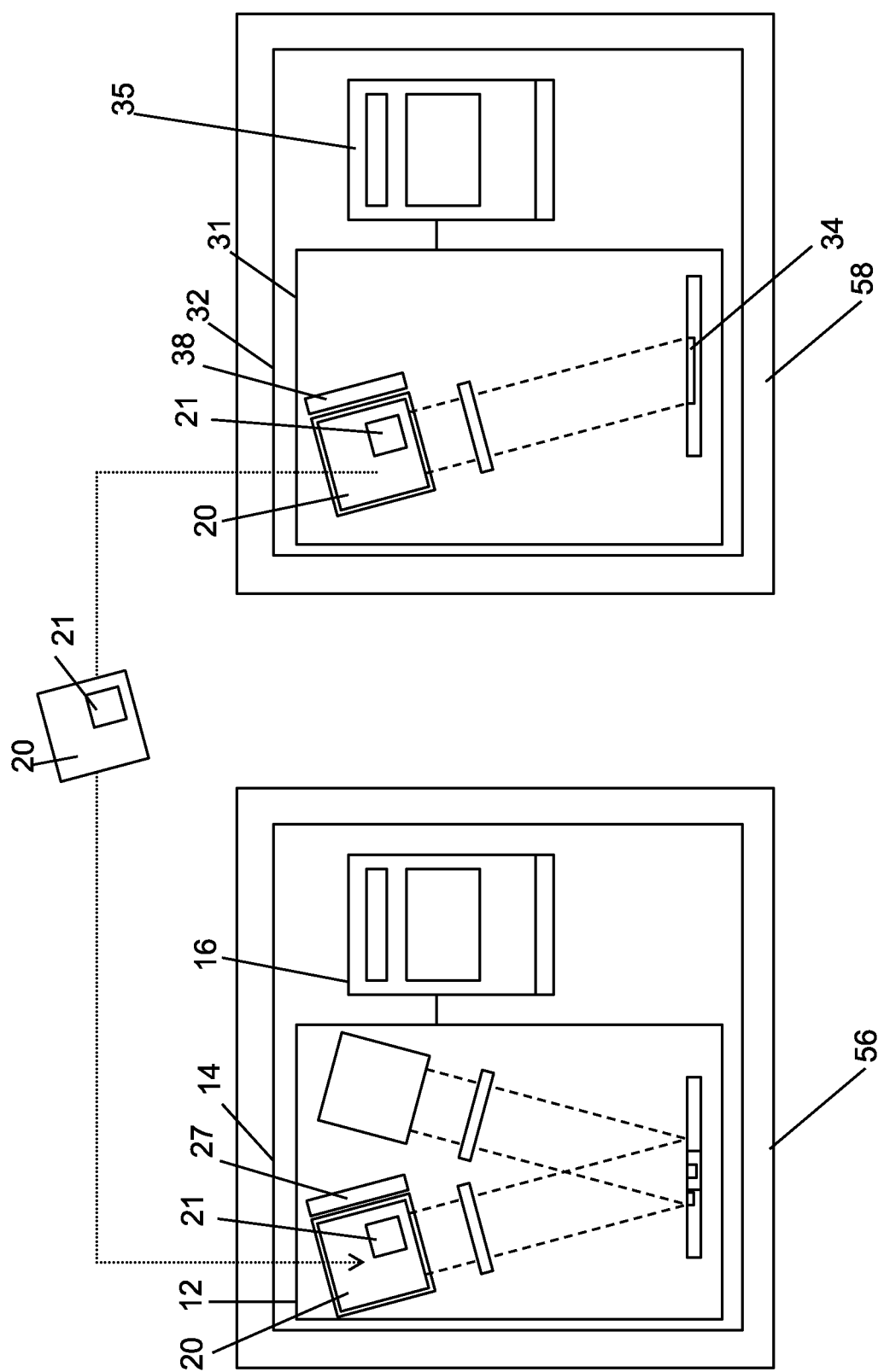
FIGS. 5A-5B show different embodiments of step a) of the method for correcting signal light intensities measured by a detector of a detection unit in a laboratory instrument. In step a) (44) of the method (42), the control device (16) of the laboratory instrument (14) receives a basic light intensity of the light source (20). The basic light intensity of the light source (20) is measured by a calibrated light sensor (34) of a light source test-system (32) which is separate from the laboratory instrument (14). For example, the laboratory instrument (14) may be located in a diagnostic laboratory (56) while the light source test-system (32) is located at a light source manufacturing facility (58). There are different ways how the control device (16) of the laboratory instrument (14) can receive the basic light intensity from the light source test-system (32) which is locally separated from the laboratory instrument (14).
Figure 5B:
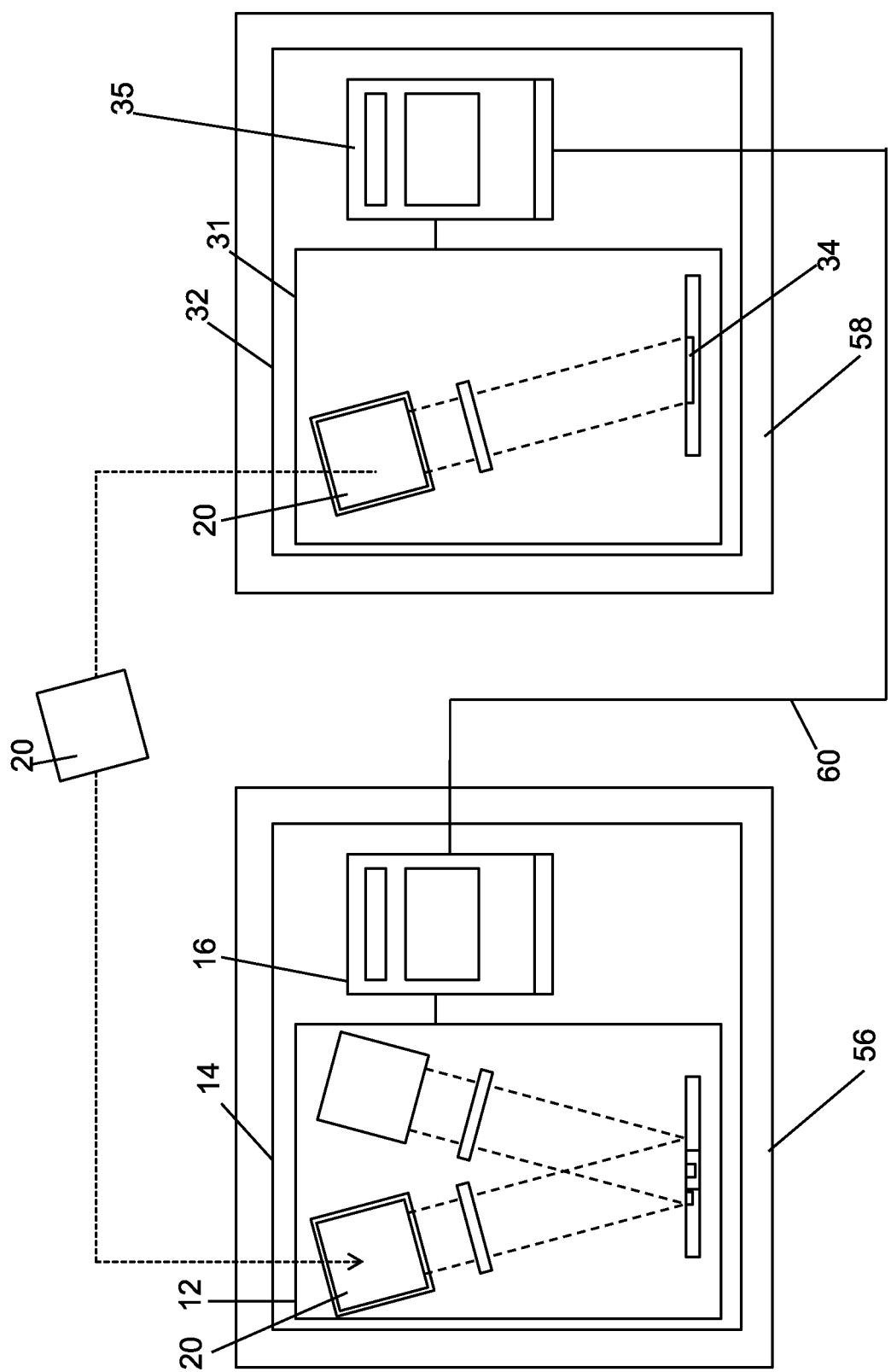

FIG. 5A-B shows different embodiments of step a) (44) of the method (42). In step a) (44) of the method (42), the control device (16) of the laboratory instrument (14) receives a basic light intensity of the light source (20). The basic light intensity of the light source (20) is measured by a calibrated light sensor (34) of a light source test-system (32) which is separate from the laboratory instrument (14). For example, the laboratory instrument (14) may be located in a diagnostic laboratory (56) while the light source test-system (32) is located at a light source manufacturing facility (58). There are different ways how the control device (16) of the laboratory instrument (14) can receive the basic light intensity from the light source test-system (32) which is locally separated from the laboratory instrument (14).

FIG. 5A shows one embodiment of step a) (44) of the method (42) where the control device (16) receives the basic light intensity from the light source test-system (32) by reading out the basic light intensity of the light source (20) from a memory (21) mounted on the light source (20) after the basic light intensity of the light source (20) was stored on said memory (21) by the light source test-system (32). As shown in FIG. 5A, the test unit (31) of the light source test-system (32) may comprise a programming or writing device (38) connected to the further control device (35) of the light source test-system (32) and configured to store the basic light intensity on a memory (21) mounted on the light source (20). Then, the light source (20) and the mounted memory (21) are transported from the light source test-system (32) to the laboratory instrument (14) as indicated by the dashed arrow and mounted in the detection unit (12) of the laboratory instrument (14) for the first time. The detection unit (12) of the laboratory instrument (14) may comprise a reading device (27) connected the control device (16) and configured to read out the basic light intensity stored in the memory (21) mounted on the light source (20).

FIG. 5B shows an alternative embodiment of step a) (44) of the method (42) where the control device (16) receives the basic light intensity from the light source test-system (32) by transmitting the basic light intensity from the light source test-system (32) to the control device (16). A light source (20) with a specific serial number is transported from the light source test-system (32) to the laboratory instrument (14) as indicated by the dashed arrow and mounted in the detection unit (12) of the laboratory instrument (14) for the first time. As shown in FIG. 5B the control device (16) of the laboratory instrument (14) and the further control device (35) of light source test-system (32) are communicatively connected to each other. And the basic light intensity may be transmitted from the light source test-system to the laboratory instrument via an internet based data transmission channel (60). The control device (16) of the laboratory instrument (14) may then associate the transmitted basic light intensity with the light source specific serial number so that the correct basic light intensity may be assigned to the light source (20) mounted in the detection unit (12) of the laboratory instrument (14).

While the current disclosure has been described in relation to its specific embodiments, it is to be understood that this description is for illustrative purposes only. It is therefore understood that numerous modifications may be made to the illustrative embodiments and that other arrangements may be devised without departing from the spirit or scope of the present disclosure as defined by the appended claims. Various publications are cited herein, the disclosures of which are incorporated herein by reference in their entireties.

LIST OF REFERENCE NUMBERS 10 detector
11 excitation filter
12 detection unit
13 emission filter
14 laboratory instrument
15 light source holder
16 control device
17 processor
18 computer-readable medium
19 user interface
20 light source
21 memory
22 sample plane
23 sample vessel
24 sample holder
26 reference light sensor
27 reading device
28 light emitted towards the sample plane
29 light emitted towards the measuring plane
30 light emitted from the sample plane
31 test unit
32 light source test-system
33 measuring plane
34 calibrated light sensor
35 further control device
36 further processor
37 further computer-readable medium
38 writing device
39 further user interface
40 further light source holder
41 equal excitation filter
42 method
44 step a) of the method
46 step b) of the method
48 step c) of the method
50 step d) of the method
52 step e) of the method
54 step f) of the method
56 diagnostic laboratory
58 light source manufacturing facility
60 data transmission channel

The invention claimed is:

1. A method to correct signal light intensities measured by a detector of a detection unit in a laboratory instrument, wherein the laboratory instrument comprises
    (i) the detection unit including
        (a) a sample plane having a sample holder for at least one sample vessel comprising a test sample to be illuminated,
        (b) a light source configured to emit light towards the sample plane,
        (c) a reference light sensor positioned in proximity to the sample holder and configured to measure:
            an initial light intensity of emitted light towards the sample plane, and
            at least one reference light intensity of emitted light towards the sample plane, and
        (d) the detector is configured to measure a signal light intensity of emitted light from the sample plane; and
    (ii) a control device,
    the method comprising the following steps:
        receiving, via the control device, a basic light intensity of the light source;
        activating, via the control device, the light source in the detection unit;
        measuring, via the reference light sensor, an initial light intensity of emitted light towards the sample plane and transmitting the measured initial light intensity to the control device;
        calculating, via the control device, a sensitivity of the reference light sensor based on the measured initial light intensity and the basic light intensity of the light source;
        measuring, via the detector, at least one signal light intensity of emitted light from the sample plane and transmitting the at least one measured signal light intensity to the control device and at the same time the reference light sensor measures at least one reference light intensity of emitted light towards the sample plane and transmits the at least one measured reference light intensity to the control device; and
        correcting, via the control device, the at least one measured signal light intensity with the at least one reference light intensity and the calculated sensitivity of the reference light sensor.

2. The method according to claim 1, wherein the basic light intensity of the light source is measured by a calibrated light sensor of a light source test-system, wherein the light source test-system is separate from the laboratory instrument, wherein the control device receives the basic light intensity of the light source when the light source is mounted in the detection unit for the first time.

3. The method according to claim 2, wherein the control device receives the basic light intensity from the light source test-system by transmitting the basic light intensity from the light source test-system to the control device or by reading out the basic light intensity of the light source from a memory mounted on the light source after the basic light intensity of the light source was stored on said memory by the light source test-system.

4. The method according to claim 1, wherein the sensitivity of the reference light sensor is the measured initial light intensity divided by the basic light intensity of the light source.

5. The method according to claim 1, wherein the basic light intensity is associated with a basic light intensity minimum acceptance value.

6. The method according to claim 5, wherein the control device further receives the basic light intensity minimum acceptance value in the receiving step, wherein the control device calculates at least one comparison value based on the at least one measured reference light intensity and the sensitivity of the reference light sensor, wherein the control device compares the basic light intensity minimum acceptance value with the at least one comparison value, wherein the control device further comprises a user interface, wherein if the at least one comparison value is smaller than the basic light intensity minimum acceptance value a warning message, an error message, or a user notification indicating that the light source needs to be exchanged is displayed on the user interface.

7. The method according to claim 6, wherein the at least one comparison value is the at least one measured reference light intensity divided by the sensitivity of the reference light sensor.

8. The method according to claim 5, wherein the basic light intensity minimum acceptance value is stored on memory mounted on the light source, wherein the control device receives the basic light intensity minimum acceptance value by reading out the basic light intensity minimum acceptance value from the memory mounted on the light source.

9. The method according to claim 2, wherein the detection unit comprises at least one excitation filter which is located between the light source and the light reference sensor, wherein the light source test-system comprises at least one equal excitation filter which is located between the light source and the calibrated light sensor of the light source test-system, wherein for each excitation filter, each of the steps of the method are conducted.

10. The method according to claim 3, wherein the light source comprises at least one light-emitting diode mounted on a printed circuit board, wherein the memory is an electrically erasable programmable read-only memory mounted on the printed circuit board.

11. The method according to claim 1, wherein the reference light sensor comprises one or more photodiodes.

12. The method according to claim 1, wherein the laboratory instrument is configured to conduct a nucleic acid amplification reaction, wherein at least one sample vessel comprising a test sample is inserted into the sample holder of the sample plane, wherein the signal light intensity emitted from the sample plane during the nucleic acid amplification reaction is measured by the detector and used to determine a presence and a concentration of an analyte of interest in the test sample.

13. The laboratory instrument adapted to execute the steps of the method according to claim 1.

14. A computer program product comprising instructions to cause the laboratory instrument to execute the steps of the method according to claim 1.

15. A non-transitory computer-readable medium having stored thereon the computer program product of claim 14.

* * * * *